US005296477A

United States Patent [19]

Taverne et al.

[11] Patent Number: 5,296,477

[45] Date of Patent: Mar. 22, 1994

[54] AMINOALKYL BENZOXAZINE AND BENZTHIAZINE COMPOUNDS HAVING A HIGH 5-$HT_{1A}$ AFFINITY

[75] Inventors: Thierry Taverne, Saint Martin les Boulogne; Isabelle Lesieur, Gondecourt; Patrick Depreux, Armentieres; Daniel H. Caignard, Paris; Béatrice Guardiola, Neuilly sur Seine Paris; Gérard Adam, Le Mesnil le Roi; Pierre Renard, Versailles, all of France

[73] Assignee: Adir et Compagnie, Courbevoie, France

[21] Appl. No.: 983,676

[22] Filed: Dec. 1, 1992

Related U.S. Application Data

[62] Division of Ser. No. 945,492, Sep. 16, 1992, which is a division of Ser. No. 765,959, Sep. 26, 1991, Pat. No. 5,196,434.

[30] Foreign Application Priority Data

Sep. 26, 1990 [FR] France ................................ 90 11866

[51] Int. Cl.[5] ................... A61K 31/535; A61K 31/54; C07D 265/36; C07D 279/16

[52] U.S. Cl. .............................. 514/224.2; 514/230.5; 544/6; 544/52; 544/70; 544/105

[58] Field of Search ....................... 544/52, 105, 6, 70; 514/224.2, 230.5

[56] References Cited

U.S. PATENT DOCUMENTS 3,770,734 11/1973 Pesson et al. ........................ 544/105
5,225,409 7/1993 Taverne et al. .................. 514/230.5

FOREIGN PATENT DOCUMENTS 0110781 6/1984 European Pat. Off. .
0171702 2/1986 European Pat. Off. .
0174811 3/1986 European Pat. Off. .
0223674 5/1987 European Pat. Off. .
0281309 9/1988 European Pat. Off. .
2035749 12/1970 France .

OTHER PUBLICATIONS

Life Sciences 49, p. 37; "Use of a Conflict Procedure in Pigeons to Characterize Anxiolytic Drug Activity: Evaluation of Activity", etc. (1991), Koek et al.
"The Pharmacological Basis of Therapeutics" by Goodman and Gilman, Eighth Edition (1990) p. 429.
J. Med. Chem. 30, 1166–1176 (1987), Weinstock et al.
Acta Ther. 13(2), 125–129 (1987), Brunet et al.
Il Farmaco 44(1), 77–88 (1989), Moussavi et al.

*Primary Examiner*—Mukund J. Shah
*Assistant Examiner*—Philip J. Datlow
*Attorney, Agent, or Firm*—Gordon W. Hueschen

[57] ABSTRACT

Compounds of general formula (I):

$$O{=}C(X\text{–}A)\text{–}N(R_1)\text{–benzo}[a,b,c,d]\text{–}(CH_2\text{—}CH_2)_n\text{—}N(R_2)(R_3) \quad (I)$$

wherein $R_1$, $R_2$, $R_3$, n, X and A are defined in the description.

Medicinal products containing the same are useful as antidepressives or anxiolytics due to their 5-HT1A receptor agonist activity.

16 Claims, No Drawings

AMINOALKYL BENZOXAZINE AND BENZTHIAZINE COMPOUNDS HAVING A HIGH 5-$HT_{1A}$ AFFINITY

This application is a division of our prior-filed copending U.S. application Ser. No. 07/945,492, filed Sep. 16, 1992, now allowed, which in turn is a division of Ser. No. 07/765,959, filed Sep. 26, 1991, now U.S. Pat. No. 5,196,434.

The present invention relates to new heterocycle-substituted alkylamines, to a process for preparing these and to pharmaceutical compositions containing them.

A large number of heterocycle-substituted alkylamines containing a benzoxazolinone, benzothiazolinone or benzoxazinone unit have already been described.

The Applicant has now discovered new heterocycle-substituted alkylamines with a totally different chemical structure which possess the property of binding with a very high affinity to 5-$HT_{1A}$ serotoninergic receptors. This affinity is coupled with an excellent specificity and that renders them usable in the treatment of diseases of the serotoninergic system, and more especially depression, stress, anxiety and schizophrenia, at lower doses than the compounds of the prior art. This feature, combined with their low toxicity, renders the compounds of the invention usable with a great safety which is especially advantageous in view of the frailty of the populations at which this type of treatment is aimed.

More specifically, the present invention relates to the compounds of general formula (I):

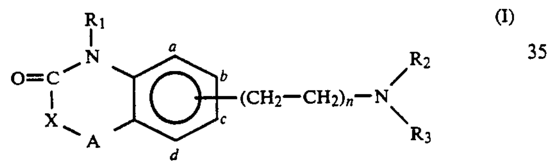

in which:

$R_1$ represents a hydrogen atom or a lower alkyl group, n represents 1 or 2,

A represents an oxygen or sulfur atom,

X represents a $CH_2$ group or a single bond, $R_2$ represents a hydrogen atom or a lower alkyl or lower acyl group while $R_3$ represents a group $(CH_2)_pR_4$, with p an integer between 1 and 6, and $R_4$ represents:

either a nitrile group, and in this case $R_3$ represents a group $(CH_2)_{p-1}R_4$ or a halogen atom or an amino group optionally substituted with:

- a (lower alkyl)sulfonyl group,
- a phenylsulfonyl group optionally substituted on the phenyl ring with one or more lower alkyl, lower alkoxy, hydroxyl or trifluoromethyl groups or a halogen atom,
- one or two ($C_1$-$C_6$) acyl groups optionally substituted with a lower alkyl, lower alkoxy or hydroxyl group, a halogen atom or a phenyl, thienyl, benzothienyl, indolyl, furyl or benzofuryl group, the phenyl, thienyl, benzothienyl, indolyl, furyl and benzofuryl groups themselves optionally being substituted with one or more lower alkyl, lower alkoxy or hydroxyl groups or a halogen atom,
- one or two linear or branched ($C_1$-$C_6$) alkyl groups, or $R_4$ represents any one of the following groups:

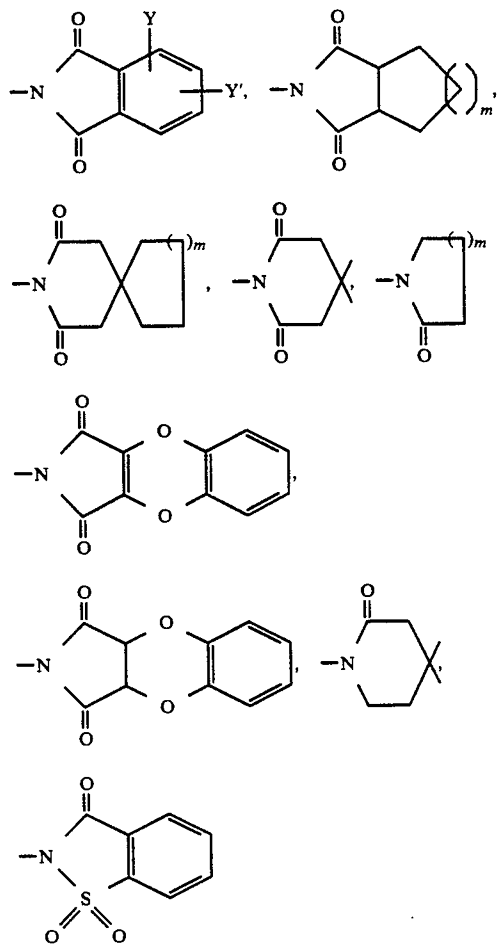

in which:

Y and Y', which may be identical or different, represent a hydrogen atom, a halogen atom or a lower alkyl, lower alkoxy or hydroxyl group, m is an integer equal to 1 or 2, their enantiomers, diastereoisomers and epimers as well as their addition salts with a pharmaceutically acceptable acid or a pharmaceutically acceptable base when $R_1$=H.

Among pharmaceutically acceptable acids, hydrochloric, sulfuric, tartaric, maleic, fumaric, oxalic, methanesulfonic, camphoric, ethanesulfonic and citric acids, and the like, may be mentioned without implied limitation. Among pharmaceutically acceptable bases, sodium, potassium and calcium hydroxides, as well as sodium, potassium and calcium carbonates, and the like, may be mentioned without implied limitation.

The invention also encompasses the process for preparing the compounds of general formula (I), wherein a derivative of formula (II):

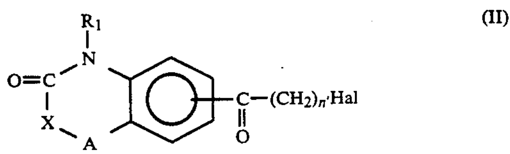

with Hal representing a halogen atom and $R_1$, A and X having the same definition as in the formula (I), and n' represents 1 or 3, is used as a starting material, which compound is treated with a trialkylsilane in an acid medium to yield a compound of formula (III):

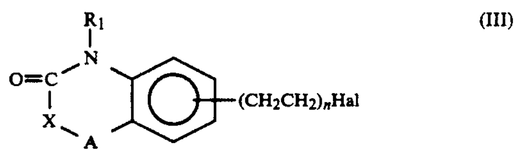

with A, X, $R_1$, n and Hal as defined above, which is condensed:

either with an amine of formula:

$$HN(R_2)(R_3) \quad \text{(IV)}$$

with $R_2$ and $R_3$ having the same definition as above, to yield a compound of formula (I):

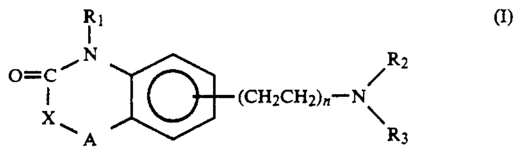

with $R_1$, X, A, n, $R_2$ and $R_3$ having the same definition as above, the isomers of which are separated, where appropriate, and purified if necessary by chromatography or crystallization, or an amine of formula:

$$H_2NR_3 \quad \text{(IV/a)}$$

in which $R_3$ has the same definition as above, to yield a compound of formula (I/a):

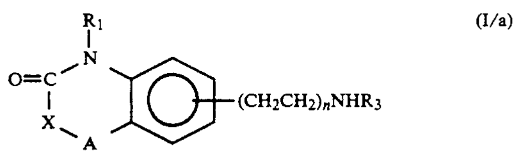

a special case of the compounds of formula (I), in which X, A, $R_1$, n and $R_3$ have the same definition as in the formula (I) and $R_2$ in this case represents a hydrogen atom, which is purified, if so desired, by chromatography and/or crystallization, the isomers of which are separated, where appropriate, and which is treated, if so desired, with a compound of formula (IV/b) in an alkaline medium:

$$Hal_a—R_2 \quad \text{(IV/b)}$$

in which $Hal_a$ represents a halogen atom and $R_2$ has the same meaning as above, to yield a compound of formula (I), which is purified if necessary by chromatography and/or crystallization and the isomers of which are separated, where appropriate, which compound of formula (I) or (I/a), irrespective of the process according to which it has been obtained, may be, if so desired, salified with a pharmaceutically acceptable acid or base.

The compounds for which $R_3$=H may be used as intermediates in the synthesis of the compounds of formula (I). In this case, the compound of formula (I/a1):

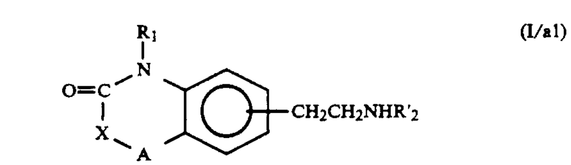

where X, $R_1$ and A have the same definition as in the formula (I) and R'2 represents a hydrogen atom or a lower alkyl group, or one of its addition salts with a pharmaceutically acceptable acid or, where appropriate, base, is treated either with a compound of formula (V):

$$R_4—(CH_2)p—Hal' \quad \text{(V)}$$

in which Hal' represents a halogen atom and $R_4$ and p have the same definition as above, in the presence of an alkaline agent, to yield a compound of formula (I/b):

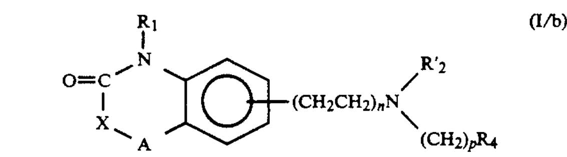

a special case of the compounds of formula (I) for which $R_1$, X, A, n, p, $R'_2$ and $R_4$ have the same meaning as above, the isomers of which compound of formula (I/b) are separated, where appropriate, which is purified, if so desired, by a technique of chromatography or of crystallization and which is treated, when $R'_2$ represents a hydrogen atom and $R_2$ a lower alkyl group, with a derivative of formula (VI):

$$R_2—Hal'' \quad \text{(VI)}$$

in which $R_2$ has the same meaning as in the formula (I) and Hal'' represents a halogen atom, to obtain a compound of formula (I), the isomers of which are separated and which is purified if necessary by a technique of chromatography or of crystallization, either with a compound of formula (V) as defined above, to yield a compound of formula (I), which is purified if necessary by chromatography and/or crystallization after separation of the isomers, where appropriate, or with a compound of formula (VII):

$$Par—(CH_2)p\text{-}1Hal''' \quad \text{(VII)}$$

in which p has the same meaning as in the formula (I), Hal''' represents a halogen atom and Par represents either a CN group or a group $CH_2Hal_4$, where Hal4 represents a halogen atom, to yield a compound of formula (I/d):

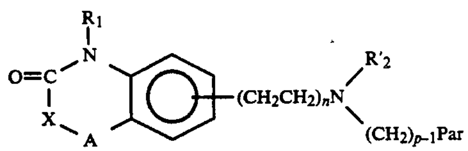

in which X, A, $R_1$, n, p, Par and $R'_2$ have the same definition as above, the isomers of which are separated, where appropriate, which is purified if necessary by chromatography and/or crystallization and which is treated, if so desired, either by catalytic hydrogenation or with an alkali metal mixed hydride in a $C_1$–$C_6$ aliphatic alcohol medium when Par Par represents a CN group, or with an excess of ammonia when Par represents a group $CH_2Hal_4$, where $Hal_4$ has the same definition as above, to yield a compound of formula (I/e):

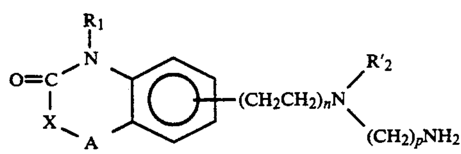

in which $R_1$, X, A, n, $R'_2$ and p have the same definition as above, the isomers of which are separated, where appropriate, which is purified, if so desired, by chromatography and/or crystallization and which is reacted with a compound of formula (VIII):

$$R'_4SO_2Hal'''' \quad (VIII)$$

in which $R'_4$ is a lower alkyl group or a phenyl group optionally substituted with one or more lower alkyl, lower alkoxy, hydroxyl or trifluoromethyl groups or a halogen atom and Hal'''' is a halogen atom, to yield a compound of formula (I/f):

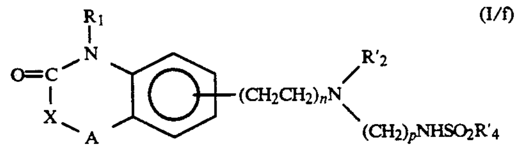

in which $R_1$, X, A, n, p, $R'_2$ and $R'_4$ have the same definition as above, the isomers of which are separated, where appropriate, and which is purified if necessary by a technique selected from crystallization and/or chromatography, which compounds of formula (I/b), (I/d), (I/e) or (I/f), irrespective of the process according to which they have been obtained, may be salified by adding a pharmaceutically acceptable base or acid.

The compounds of formula (I) possess advantageous pharmacological properties.

Binding tests showed that the compounds of the invention behave as very potent ligands of $5\text{-HT}_{1A}$ receptors. This affinity is accompanied by a very great selectivity with respect to other receptors, in particular $D_2$ and $\alpha_2$, in contrast to the behavior observed with the compounds of the prior art.

The compounds of the invention are of low toxicity, and possess good activity in the pigeon conflict test, confirming the activity detected by binding. Some of them possess, moreover, an excellent analgesic activity, others a noteworthy hypnotic, antihypertensive or normolipemic activity.

The compounds of the invention hence find their application in the treatment of distress, anxiety, depression, schizophrenia, psychoses, dementia, senile dementia, aggressiveness and agitation, but also, for some of the compounds, in painful manifestations in all their forms, sleep disorders, arterial hypertension, glaucoma and the prevention of atheroma.

The subject of the present invention is also pharmaceutical compositions containing as active principle at least one compound of general formula (I) or one of its addition salts with a pharmaceutically acceptable acid or, where appropriate, with a pharmaceutically acceptable base, alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like.

The dosage varies according to the patient's age and weight and the nature and severity of the condition, as well as the administration route. The latter may be oral, nasal, rectal or parenteral.

Generally speaking, single doses range between 0.05 and 30 mg for conditions affecting mental behavior and between 1 mg and 500 mg for the treatment of pain and of arterial hypertension, that is to say, taken in one to three doses per 24 hours.

The examples which follow illustrate the invention and in no way limit the latter.

The 1H nuclear magnetic resonance spectra were recorded using TMS (tetramethylsilane) as an internal reference. The chemical shifts are expressed in parts per million (ppm). The infrared spectra were run in the form of a potassium bromide disk containing approximately 1% of the product to be analyzed.

The preparations do not form part of the invention, but are useful for carrying out the synthesis of the compounds of the invention.

PREPARATION 1

6-(Bromoacetyl)benzothiazolinone 210 g (1.60 mol) of aluminum chloride are introduced into a 500-$cm^3$ ground-necked flask surmounted by a condenser, and 43 $cm^3$ of dimethylformamide are then added dropwise and with magnetic stirring via a dropping funnel. 30.2 g (0.2 mol) of benzothiazolinone are then added and, while the reaction medium homogenizes, the temperature is stabilized at 70° C. using an oil bath. 19.8 $cm^3$ (0.24 mol) of bromoacetyl chloride are then introduced gradually. After the addition, the mixture is left stirring for one hour at a temperature of 70° C. The reaction medium is hydrolyzed by pouring it onto crushed ice and the precipitate obtained is drained, washed copiously with water and dried. The product is recrystallized in dioxane.

Yield: 65%

Melting point: 235° C. with decomposition

PREPARATION 2

6-(2-Bromoethyl)benzothiazolinone

In a 500-$cm^3$ ground-necked flask surmounted by a condenser, and placed in an oil bath, 40.8 g (0.15 mol) of 6-(bromoacetyl)benzothiazolinone are dissolved in 90 $cm^3$ of trifluoroacetic acid with magnetic stirring and while the temperature is stabilized at 60° C. 52.7 $cm^3$ (0.33 mol) of triethylsilane are introduced dropwise via a dropping funnel. After the addition, the heating is stopped and the mixture is then left stirring vigorously for 30 hours. The reaction medium is hydrolyzed by pouring it into ice-cold water, and the precipitate obtained is drained and washed with water until the filtrate is neutral and then with hexane. The product is dried and recrystallized in absolute ethanol.

Yield: 80%

Melting point: 179°-180° C.

PREPARATION 3

3-Methylbenzothiazolinone

In a 2-liter flask, 75.6 g (0.5 mol) of benzothiazolinone are dissolved in a solution containing 20 g of sodium hydroxide (0.5 mol) in approximately 800 $cm^3$ of water. The solution is filtered. With magnetic stirring, 47.5 $cm^3$ of methylsulfate (0.5 mol) are introduced dropwise with a dropping funnel. After the addition, the mixture is left stirring for 20 hours at room temperature. The medium is alkalinized with a slight excess of sodium hydroxide and left stirring for one hour. The precipitate obtained is drained and washed with water until the filtrate is neutral. The product is dried. It is recrystallized in propanol.

Yield: 88%

Melting point: 72°-74° C.

PREPARATION 4

3-Methyl-6-(bromoacetyl)benzothiazolinone 210 g (1.60 mol) of aluminum chloride are introduced into a 500-$cm^3$ ground-necked flask surmounted by a condenser, and 43 $cm^3$ of dimethylformamide are then added dropwise and with magnetic stirring via a dropping funnel. 33 g (0.20 mol) of 3-methylbenzothiazolinone are then added and, while the reaction medium homogenizes, the temperature is stabilized at 70° C. using an oil bath. 19.8 $cm^3$ (0.24 mol) of bromoacetyl chloride are then added gradually. After the addition, the mixture is left stirring for one hour at a temperature of 70° C. The reaction medium is hydrolyzed by pouring it onto crushed ice and the precipitate obtained is drained, washed with water until the filtrate is neutral and dried. The product is recrystallized in 95° strength alcohol.

Yield: 66%

Melting point: 164°-165° C.

PREPARATION 5

3-Methyl-6-(2-bromoethyl)benzothiazolinone

In a 500-$cm^3$ ground-necked flask surmounted by a condenser and placed in an oil bath, 42.9 g (0.15 mol) of 3-methyl-6-(bromoacetyl)benzothiazolinone are dissolved in 77 $cm^3$ of trifluoroacetic acid with magnetic stirring and while the temperature is stabilized at 60° C. 52.7 $cm^3$ (0.33 mol) of triethylsilane are introduced dropwise via a dropping funnel. After the addition, the heating is stopped and the mixture is left stirring vigorously for 30 hours. The reaction medium is hydrolyzed by pouring it into ice-cold water, and the precipitate obtained is drained and washed with water until the filtrate is neutral and then with hexane. The product is dried and recrystallized in cyclohexane.

Yield: 86%

Melting point: 97°-98° C.

PREPARATION 6

7-(Bromoacetyl)benzoxazinone 0.01 mol of 7-acetylbenzoxazinone, described in Application EP 223,674, is dissolved in 100 $cm^3$ of methylene chloride. 0.011 mol of bromine is added dropwise and with stirring via a dropping funnel, and stirring is maintained for 13 hours. The mixture is filtered and evaporated to dryness and the residue is recrystallized.

PREPARATION 7

6-(2-Bromoethyl)-3-oxo-2,3-dihydro-1,4-benzoxazine

This product is advantageously obtained either by catalytic hydrogenation of 6-(bromoacetyl)-3-oxo-2,3-dihydro-1,4-benzoxazine, described in French Patent Application 2,035,749, in an acetic acid medium in the presence of palladinized charcoal, or by the action of trialkylsilane on this compound in a trifluoroacetic acid medium.

PREPARATION 8

4-Methyl-7-(2-bromoethyl)-3-oxo-2,3-dihydro-1,4-benzoxazine 0.01 mol of 4-methyl-7-acetyl-3-oxo-2,3-dihydro-1,4-benzoxazine, obtained in European Patent Application 0,223,674, is dissolved in methylene chloride. 0.012 mol of bromine is added with stirring via a dropping funnel.

Stirring is maintained for two hours, and the reaction medium is then left in a oil bath at 40° C. with stirring for 2 hours. The mixture is filtered. The solvent is evaporated off. The residue is recrystallized.

The 4-methyl-7-(bromoacetyl)-3-oxo-2,3-dihydrobenzoxazine is converted to 4-methyl-7-(2-bromoethyl)-3-oxo-2,3-dihydro-1,4-benzoxazine by catalytic hydrogenation in an acetic acid medium in the presence of palladinized charcoal, or by the action of trialkylsilane in a trifluoroacetic acid medium.

PREPARATION 9

6-(2-Propylaminoethyl)-3-oxo-2,3-dihydro-1,4-benzoxazine

In a round-bottomed flask equipped with a mechanical stirrer and a calcium chloride guard tube, 0.01 mol of n-propylamine and 0.015 mol of triethylamine are added to a solution of 6-(2-bromoethyl)-3-oxo-2,3-dihydro-1,4-benzoxazine in 40 $cm^3$ of dimethylformamide. The mixture is heated to reflux for 15 hours and the precipitate formed is drained in the heated state. The residue is evaporated under vacuum and the product is recrystallized.

PREPARATION 10

6-(4-Bromobutyl)benzothiazolinone

Using the procedure described in Preparation 2, but replacing 6-(bromoacetyl)benzothiazolinone by 6-(4-bromobutyryl)benzothiazolinone, the product of the title is obtained.

PREPARATION 11

3-Methyl-6-(4-bromobutyl)benzothiazolinone

Using the procedure described in Preparation 5, but replacing 6-(bromoacetyl)-3-methylbenzothiazolinone by 3-methyl-6-(4-bromobutyryl)benzothiazolinone, the product of the title is obtained.

PREPARATION 12

7-(4-Bromobutyl)-4-methyl-2,3-dihydro-3-oxobenzoxazine

Using the procedure described in Preparation 2, but replacing 6-(bromoacetyl)benzothiazolinone by 7-(4-bromobutyryl)-4-methyl-2,3-dihydro-3-oxobenzoxazine, described in Application EP 0,223,674, the product of the title is obtained.

PREPARATION 13

6-(4-Bromobutyl)benzoxazolinone

Using the procedure described in Preparation 2, but replacing 6-(bromoacetyl)benzothiazolinone by 6-(4-bromobutyryl)benzoxazolinone, described in Patent Application EP 0,281,309, the product of the title is obtained.

PREPARATION 14

3-Methyl-6-(4-bromobutyl)benzoxazolinone

Using the procedure described in Preparation 13, but replacing 6-(4-bromobutyryl)benzoxazolinone by 3-methyl-6-(4-bromobutyryl)benzoxazolinone, the product of the title is obtained.

EXAMPLE 1

3-Methyl-6-(2-aminoethyl)benzothiazolinone (hydrochloride)

In a 250 $cm^3$ ground-necked flask, 8.1 g (0.03 mol) of 3-methyl-6-(2-bromoethyl)benzothiazolinone and 0.9 g of potassium iodide are dissolved in 120 $cm^3$ of methanol and 30 $cm^3$ of chloroform. A stream of gaseous ammonia is bubbled into the solution to the point of saturation, equivalent to approximately 2.6 g of ammonia, and a reflux condenser is then fitted. The temperature is stabilized at 50° C. with an oil bath and the mixture is left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized in absolute ethanol.

Yield: 32%

Melting point: 228°-230° C.

Molecular weight: 244.75 g/mol

Percentage composition: Calculated: C 49.07; H 5.35; N 11.45. Found: C 49.17; H 5.38; N 11.48.

Infrared spectrometry: 3100-2800 $cm^{-1}$: $\nu$(C—H). 2750-2400 $cm^{-1}$: $\nu$(NH+). 1680 $cm^{-1}$: $\nu$(C=O) —O—CO—NR—. 1600-1580 $cm^{-1}$: $\nu$(C=C) aromatic.

Nuclear magnetic resonance spectrometry: Solvent: DMSO-$d_6$. $\delta$=3.00 ppm unresolved peaks; (4H). $\delta$=3.38 ppm singlet; (3H) $NCH_3$. $\delta$=7.28 ppm unresolved peaks; (2H) H4,5 aromatic. $\delta$=7.55 ppm unresolved peaks; (1H) H7 aromatic. $\delta$=8.17 ppm signal; (3H) ($NH_3$+).

The base is obtained by dissolution of the hydrochloride in water, alkalinization and three extractions with chloroform. The chloroform phases are combined, dried over calcium chloride and evaporated to dryness. The residue may be used without further purification as a starting material.

EXAMPLE 2

3-Methyl-6-{2-[N-(4-phthalimidobutyl)amino]ethyl}benzothiazolinone

In a round-bottomed flask, 2.2 mmol of 3-methyl-6-(2-aminoethyl)benzothiazolinone, obtained in the previous example, are dissolved in 20 ml of dimethyl-formamide in the presence of 2.4 mmol of N-(4-bromobutyl)phthalimide, 6.6 mmol of potassium carbonate and a catalytic amount of potassium iodide. The mixture is left stirring at 60° C. for 6 hours. After cooling, the solvent is evaporated off and/or extracted with chloroform after adding water.

After washing, drying and evaporation of the organic phase, the expected product is obtained after purification by chromatography on a silica column, followed by crystallization.

$^1H$ Nuclear Magnetic Resonance: Solvent: DMSO-$d_6$. $\delta$=1.75 ppm N—$(CH_2)_2$—$CH_2$—$CH_2$-phthalimido 2H, multiplet. $\delta$=3.38 ppm 3H, $CH_3$ singlet; (3H) $NCH_3$. $\delta$=3.62 ppm N—$(CH_2)_3$—$CH_2$-phthalimido 2H, triplet.

Infrared: 3100-2800 $cm^{-1}$: $\nu$CH. 1680 $cm^{-1}$: $\nu$CO (SCON).

EXAMPLE 3

3-Methyl-6-{2-[N-(4-phthalimidobutyl)-N-n-propylamino]ethyl}benzothiazolinone 1.5 mmol of 3-methyl-6-{2-[N-(4-phthalimidobutyl)amino]ethyl}benzothiazolinone, obtained in Example 2, is dissolved in 15 ml of dimethylformamide in the presence of 4.4 mmol of 1-iodopropane and 4.4 mmol of potassium carbonate. After 24 hours' stirring at 60° C., the solvent is evaporated off and the reaction medium is taken up with 10 ml of water and extracted with chloroform. The organic phase is dried and evaporated and the expected product is obtained after purification by chromatography on a silica column, followed by crystallization.

$^1H$ Nuclear Magnetic Resonance: Solvent: DMSO-$d_6$. $\delta$=0.88 ppm N—$(CH_2)_2$—$CH_3$; triplet (3H). $\delta$=1.75 ppm N—$(CH_2)_2$—$CH_2$—$CH_2$-phthalimido; (2H), multiplet. $\delta$=3.38 ppm (3H), N—$CH_3$, singlet. $\delta$=3.62 ppm N—$(CH_2)_3$—$CH_2$-phthalimido (2H), triplet.

Infrared: 3100-2800 $cm^{-1}$: $\nu$CH. 1680 $cm^{-1}$: $\nu$CO (SCON).

EXAMPLE 4

3-Methyl-6-{2-[N-(3-phthalimidopropyl)amino]ethyl}benzothiazolinone

Using the procedure described in Example 2, but replacing N-(4-bromobutyl)phthalimide by N-(3-bromopropyl)phthalimide, the product of the title is obtained.

$^1H$ Nuclear Magnetic Resonance: Solvent: DMSO-$d_6$. $\delta$=3.38 ppm, 3H, $CH_3$, singlet, N—$CH_3$. $\delta$=3.78 ppm, 2H, N$(CH_2)_2$—$CH_2$-phthalimido.

Infrared: 3100–2800 $cm^{-1}$: νCH. 1680 $cm^{-1}$: νCO (SCON).

EXAMPLE 5

3-Methyl-6-{2-[N-(3-phthalimidopropyl)-N-n-propylamino]ethyl}benzothiazolinone

Using the procedure described in Example 3, but replacing 3-methyl-6-{2-[N-(4-phthalimidobutyl-)amino]-ethyl}benzothiazolinone by 3-methyl-6-{2-[N-(3-phthalimidopropyl)amino]ethyl}benzothiazolinone, obtained in Example 4, the expected product is obtained.

$^1$H Nuclear Magnetic Resonance: Solvent: DMSO-d6. δ=0.89 ppm, 3H, N—$CH_2$—$CH_2$—$CH_3$, triplet. δ=3.38 ppm, 3H, N—$CH_3$, singlet.

Infrared: 3100–2800 $cm^{-1}$: νCH. 1680 $cm^{-1}$: νCO (SCON).

EXAMPLE 6

3-Methyl-6-{2-[N-(2-phthalimidoethyl)amino]ethyl} benzothiazolinone

Using the procedure described in Example 2, but replacing N-(4-bromobutyl)phthalimide by N-(2-bromoethyl)phthalimide and leaving the reactants stirring for 40 hours, the expected product is obtained. $^1$H Nuclear Magnetic Resonance: Solvent: DMSO-$d_6$. δ=3.39 ppm, 3H, $CH_3$, singlet, N-$CH_3$. δ=3.80 ppm, 2H, $N(CH_2)_2$—$CH_2$-phthalimido.

Infrared: 3100–2800 $cm^{-1}$: νCH. 1680 $cm^{-1}$: νCO (SCON).

EXAMPLE 7

3-Methyl-6-{2-[N-(2-phthalimidoethyl)-N-n-propylamino]-ethyl}benzothiazolinone

Using the procedure described in Example 3, but replacing 3-methyl-6-{2-[N-(4-phthalimidobutyl-)amino]-ethyl}benzothiazolinone by 3-methyl-6-{2-[N-(2-phthalimidoethyl)amino]ethyl}benzothiazolinone, the product of the title is obtained.

$^1$H Nuclear Magnetic Resonance: Solvent: DMSO-$d_6$. δ=3.39 ppm, 3H, $CH_3$, singlet, N—$CH_3$.

Infrared: 3100–2800 $cm^{-1}$: νCH. 1680 $cm^{-1}$: νCO (SCON).

EXAMPLE 8

3-[4-{N-[2-(3-methylbenzothiazolinon-6-yl)ethyl-]amino}butyl]-2,4-dioxo-3-azaspiro[4.5]decane Using the procedure described in Example 2, but replacing N-(4-bromobutyl)phthalimide by N-(4-bromo-butyl)-2,4-dioxo-3-azaspiro[4.5]decane and leaving the reactants stirring for 24 hours, the product of the title is obtained.

$^1$H Nuclear Magnetic Resonance: Solvent: DMSO-$d_6$. δ=2.59 ppm, 4H, singlet, $N(CO—CH_2)_2$. δ=3.50 ppm, 3H, singlet, N—$CH_3$.

Infrared: 3000–2800 $cm^{-1}$: νCH. 1600–1680 $cm^{-1}$: νCO (overlapping).

EXAMPLE 9

3-[4-{N-[2-(3-methylbenzothiazolinon-6-yl)ethyl]-N-propylamino}butyl]-2,4-dioxo-3-azaspiro[4.5]decane Using the procedure described in Example 3, but replacing the compound obtained in Example 2 by the compound obtained in Example 8, the product of the title is obtained.

EXAMPLE 10

3-[4-{N-[2-(3-methylbenzothiazolinon-6-yl)ethyl-]amino}butyl]-2,4-dioxo-3-azabicyclo[3.3.0]octane Using the procedure described in Example 2, but replacing N-(4-bromobutyl)phthalimide by N-(4-bromobutyl)-2,4-dioxo-3-azabicyclo[3.3.0]octane and leaving the reactants stirring for 24 hours, the product of the title is obtained.

1H Nuclear Magnetic Resonance: Solvent: DMSO-$d_6$. δ=3.39 ppm, 3H, N—$CH_3$. δ=3.49 ppm, 2H, triplet, $CH_2$—N (azabicyclooctane).

Infrared: 3100–2800 $cm^{-1}$: νCH. 1680 $cm^{-1}$: νCO (SCON).

EXAMPLE 11

3-Methyl-6-[2-{N-[4-(4,4-dimethyl-2,6-dioxo-1-piperidyl)butyl]amino}ethyl]benzothiazolinone Using the procedure described in Example 2, but replacing N-(4-bromobutyl)phthalimide by N-(4-bromobutyl)-4,4-dimethyl-2,6-dioxopiperidine and leaving the reactants stirring for 24 hours, the expected product is obtained.

$^1$H Nuclear Magnetic Resonance: Solvent: DMSO-$d_6$. δ=1.06 ppm, 6H, singlet $C(CH_3)_2$. δ=3.39 ppm, N—$CH_3$, 3H, singlet.

Infrared: 1680 $cm^{-1}$: νCO (SCON).

EXAMPLE 12

3-Methyl-6-[2-{N-[4-(4,4-dimethyl-2-oxo-1-piperidyl)-butyl]amino}ethyl]benzothiazolinone Using the procedure described in Example 2, but replacing N-(4-bromobutyl)phthalimide by 1-(4-bromobutyl)-4,4-dimethyl-2-oxopiperidine and leaving the reactants stirring for 24 hours, the expected product is obtained.

EXAMPLE 13

3-Methyl-6-[2-{N-[4-(2-oxo-1-piperidyl)butyl]amino}-ethyl]benzothiazolinone

Using the procedure described in Example 2, but replacing N-(4-bromobutylphthalimide) by 1-(4-bromobutyl)-2-oxopiperidine and leaving the reactants stirring for 24 hours, the expected product is obtained.

EXAMPLE 14

3-Methyl-6-[2-(N-methyl-N-benzylamino)ethyl]benzothiazolinone 0.04 mol of N-methyl-N-benzylamine and 0.02 mol of 3-methyl-6-(2-bromoethyl)benzothiazolinone, the latter being dissolved beforehand in 120 $cm^3$ of dioxane, are introduced into a 100-$cm^3$ ground-necked flask fitted with a reflux condenser. The mixture is heated to reflux for 96 hours with magnetic stirring. After cooling, the reaction mixture is filtered and the filtrate is then evaporated on a water bath under vacuum. The residue is taken up with 50 $cm^3$ and alkalinized with 10 $cm^3$ of normal sodium hydroxide solution.

The mixture is extracted three times with 60 $cm^3$ of chloroform. The organic solutions are combined, dried over calcium chloride, filtered and evaporated on a water bath under vacuum. The residue is taken up with petroleum ether, drained, dried and recrystallized.

$^1$H Nuclear Magnetic Resonance: Solvent: DMSO-$d_6$. δ=2.22 ppm, N—$CH_3$($CH_2$—N—$CH_3$), singlet 3H.

$\delta$=3.37 ppm, N—$CH_3$ (benzothiazolinone), singlet 3H. $\delta$=3.53 ppm, N—$CH_2$—$C_6H_5$, 2H, singlet.

EXAMPLE 15

3-Methyl-6-[2-(N-methylamino)ethyl]benzothiazolinone (hydrochloride)

Using the procedure described in Example 1, but replacing ammonia by N-methylamine, the product of the title is obtained.

[1]H Nuclear Magnetic Resonance: Solvent: $D_2O$ (hydrochloride). $\delta$=2.84 ppm, singlet 3H, N—$\underline{CH_3}$. $\delta$=3.29 ppm, singlet 3H, N—$CH_3$.

Infrared: 3100–2600 $cm^{-1}$: $\nu$NH and $\nu$CH. 1680 $cm^{-1}$: $\nu$CO (SCON).

EXAMPLE 16

3-Methyl-6-(2-propylaminoethyl)benzothiazolinone hydrochloride

Using the procedure described in Example 16, but replacing isopropylamine by n-propylamine, the product of the title is obtained.

Spectral characteristics:

Infrared: 3100–2650 $cm^{-1}$: $\nu$NH and $\nu$CH. 1680 $cm^{-1}$: $\nu$CO (SCON).

EXAMPLE 17

3-Methyl-6-[2-(N-methyl-N-cyanomethylamino)ethyl]-benzothiazolinone

In a round-bottomed flask, 6.8 mmol of 3-methyl-6-[2-(N-methylamino)ethyl]benzothiazolinone -(N-methylamino)ethyl]benzothiazolinone are dissolved in 50 ml of dioxane in the presence of 20 mmol of chloroacetonitrile, 20 mmol of potassium carbonate and a catalytic amount of potassium iodide. The mixture is stirred at 60° C. for 48 hours. After cooling, the solvent is evaporated off and the reaction mixture is extracted with chloroform after adding water. After washing, drying and evaporation of the organic phase, the expected product is obtained after purification by chromatography on a silica column, followed by crystallization.

[1]H Nuclear Magnetic Resonance, DMSO-$d_6$. $\delta$=3.39 ppm, singlet, 3H, N—$CH_3$.

Infrared: 1680 $cm^{-1}$: $\nu$CO (SCON).

EXAMPLE 18

3-Methyl-6-{2-[N-methyl-N-(2-aminoethyl)amino]ethyl}benzothiazolinone

In a ground-necked flask, 6 mmol of 3-methyl-6-[2-(N-methylamino)ethyl]benzothiazolinone are dissolved in 50 ml of dioxane, 20 mmol of 1-chloro-2-bromoethane and 20 mmol of potassium carbonate. The mixture is stirred for 48 hours at a temperature of 60° C. After cooling, the mixture is evaporated and the reaction medium is extracted with chloroform after adding water. After washing, drying and evaporation of the organic phase, 3-methyl-6-{2-[N-methyl-N-(2-chloroethyl)amino]ethyl}benzothiazolinone is obtained, which product is transferred to a ground-necked flask. A catalytic amount of potassium iodide, 25 $cm^3$ of methanol and 10 $cm^3$ of chloroform are added. A stream of gaseous ammonia is bubbled into the solution to the point of saturation and a reflux condenser is then fitted. The temperature is stabilized at 50° C. with an oil bath and the mixture is then left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized.

[1]H Nuclear Magnetic Resonance: $\delta$=3.38 ppm, singlet, 3H, N—$CH_3$.

Infrared: 1680 $cm^{-1}$: $\nu$CO (SCON).

EXAMPLE 19

3-Methyl-6-[2-{N-methyl-N-[2-(para-tolylsulfonylamino)ethyl]amino}ethyl]benzothiazolinone 4 mmol of 3-methyl-6-{2-[N-methyl-N-(2-aminoethyl)amino]ethyl}benzothiazolinone, obtained in Example 19, are dissolved in 50 ml of dichloromethane cooled in ice, and 11.4 mmol of triethylamine are added dropwise, followed by 4 mmol of tosyl chloride dissolved in dichloromethane.

The mixture is left stirring for 30 minutes at room temperature. The solvent is then evaporated off and the expected product is obtained after purification by chromatography on a silica column.

Nuclear Magnetic Resonance: 1H ($CDCl_3$). $\delta$=3.39 ppm, singlet, 3H, N—$CH_3$.

Infrared: 1680 $cm^{-1}$: $\nu$CO (SCON).

EXAMPLE 20

3-Methyl-6-[2-(N-propyl-N-cyanomethylamino)ethyl]-benzothiazolinone

Using the procedure described in Example 18, but replacing 3-methyl-6-[2-(N-methylamino)ethyl]benzothiazolinone by 3-methyl-6-[2-(N-propylamino)ethyl]-benzothiazolinone, the product of the title is obtained.

Nuclear Magnetic Resonance: 1H ($CDCl_3$). $\delta$=3.39 ppm, singlet, 3H, N—$CH_3$.

Infrared: 1680 $cm^{-1}$: $\nu$CO (SCON).

EXAMPLE 21

3-Methyl-6-{2-[N-propyl-N-(2-aminoethyl)amino]ethyl}benzothiazolinone

Using the procedure described in Example 19, but replacing 3-methyl-6-[2-(N-methyl-N-cyanomethylamino)-ethyl]benzothiazolinone by 3-methyl-6-[2-(N-propyl-N-cyanomethylamino)ethyl]benzothiazolinone, the product of the title is obtained.

EXAMPLE 22

3-Methyl-6-[2-{N-propyl-N-[2-(para-tolylsulfonylamino)ethyl]amino}ethyl]benzothiazolinone Using the procedure described in Example 20, but replacing 3-methyl-6-{2-[N-methyl-N-(2-aminoethyl)amino]ethyl}benzothiazolinone by 3-methyl-6-{2-[N-propyl-N-(2-aminoethyl)amino]ethyl}benzothiazolinone, the product of the title is obtained.

EXAMPLE 23

3-Methyl-6-[2-{N-propyl-N-[3-para-tolylsulfonylamino)-propyl]amino}ethyl]benzothiazolinone Using the procedure described in Example 19, but replacing 1-chloro-2-bromoethane by 1-chloro-3-bromopropane and 3-methyl-6-[2-(N-methylamino)ethyl]benzothiazolinone by 3-methyl-6-[2-(N-n-propylamino)ethyl]-benzothiazolinone, 3-methyl-6-{2-[N-methyl-N-(3-aminopropyl)amino]ethyl}benzothiazolinone is obtained, which product is treated as in Example 20 with tosyl chloride to yield the product of the title.

Nuclear Magnetic Resonance: 1H ($CDCl_3$). $\delta=3.38$ ppm, singlet, 3H, N—$CH_3$ Infrared: 1760 $cm^{-1}$: $\nu$CO (SCON).

EXAMPLE 24

3-Methyl-6-[2-{N-propyl-N-[4-(para-tolylsulfonylamino)-butyl]amino}ethyl]benzothiazolinone Using the procedure described in Example 24, but replacing 1-chloro-3-bromopropane by 1-chlorobromobutane, the product of the title is obtained.

EXAMPLE 25

3-Methyl-6-(4-aminobutyl)benzothiazolinone (hydrochoride)

Using the procedure described in Example 1, but replacing 3-methyl-6-(2-bromoethyl)benzothiazolinone by 3-methyl-6-(4-chlorobutyl)benzothiazolinone, 3-methyl-6-(4-aminobutyl)benzothiazolinone (hydrochloride) is obtained.

EXAMPLES 26 TO 37

Using the procedure described in Examples 2 to 13, but replacing 3-methyl-6-(2-aminoethyl)benzothiazolinone by 3-methyl-6-(4-aminobutyl)benzothiazolinone of Example 33, the following are obtained:

EXAMPLE 26

3-Methyl-6-{4-[N-(4-phthalimidobutyl)amino]butyl}benzothiazolinone

EXAMPLE 27

3-Methyl-6-{4-[N-(4-phthalimidobutyl)-N-n-propylamino]butyl}benzothiazolinone

EXAMPLE 28

3-Methyl-6-{4-[N-(3-phthalimidopropyl)amino]-butyl}benzothiazolinone

EXAMPLE 29

3-Methyl-6-{4-[N-(3-phthalimidopropyl)-N-propylamino]butyl}benzothiazolinone

EXAMPLE 30

3-Methyl-6-{4-[N-(2-phthalimidoethyl)-N-n-propylamino]butyl }benzothiazolinone

EXAMPLE 31

3-Methyl-6-{4-[N-(2-phthalimidoethyl)amino]butyl}benzothiazolinone

EXAMPLE 32

3-[4-{N-[4-(3-methylbenzothiazolinon-6-yl)butyl]amino}-butyl]-2,4-dioxo-3-azaspiro[4.5]decane

EXAMPLE 33

3-[4-{N-[4-(3-methylbenzothiazolinon-6-yl)butyl]-N-n-propylamino}butyl]-2,4-dioxo-3-azaspiro[4.5]decane

EXAMPLE 34

3-[4-{N-[4-(3-methylbenzothiazolinon-6-yl)butyl]amino}-butyl]-2,4-dioxo-3-azabicyclo[3.3.0.]octane

EXAMPLE 35

3-Methyl-6-[4-{N-[4-(4,4-dimethyl-2,6-dioxo-1-piperidyl)-butyl]amino}butyl]benzothiazolinone

EXAMPLE 36

3-Methyl-6-[4-{N-[4-(4,4-dimethyl-2-oxo-1-piperidyl)-butyl]amino}butyl]benzothiazolinone

EXAMPLE 37

3-Methyl-6-[4-{N-[4-(2-oxo-1-piperidyl)butyl]amino}butyl]benzothiazolinone

EXAMPLE 38

3-Methyl-6-[4-(N-methyl-N-benzylamino)butyl]benzothiazolinone

Using the procedure described in Example 14, but replacing 3-methyl-6-(2-bromoethyl)benzothiazolinone by 3-methyl-6-(4-bromobutyl)benzothiazolinone, the product of the title is obtained.

EXAMPLE 39

3-Methyl-6-[4-(N-methylamino)butyl]benzothiazolinone

Using the procedure described in Example 15, but replacing 3-methyl-6-[2-(N-methyl-N-benzylamino)ethyl]benzothiazolinone by 3-methyl-6-[4-(N-methyl-N-benzylamino)butyl]benzothiazolinone, obtained in the previous example, the product of the title is obtained.

EXAMPLES 40 TO 42

Using the procedure described in Examples 18 to 20, but replacing 3-methyl-6-[2-(N-methylamino)ethyl]benzothiazolinone by 3-methyl-6-[4-(N-methylamino)-butyl]benzothiazolinone, the following are obtained:

EXAMPLE 40

3-Methyl-6-[4-(N-methyl-N-cyanomethylamino)-butyl]benzothiazolinone

EXAMPLE 41

3-Methyl-6-{4-[N-methyl-N-(2-aminoethyl)amino]-butyl}benzothiazolinone

EXAMPLE 42

3-Methyl-6-[4-{N-methyl-N-[2-(para-tolylsulfonylamino)ethyl]amino}butyl]benzothiazolinone

EXAMPLE 43

7-{2-[N-(4-phthalimidobutyl)amino]ethyl}benzothiazolinone

Using the procedure described in Example 2, but replacing 3-methyl-6-(2-aminoethyl)benzothiazolinone by 7-(2-aminoethyl)benzothiazolinone, described in Example 8 of European Patent Application 174,811, the product of the title is obtained.

Using the same procedure as in Examples 3 to 13, but employing 7-(2-aminoethyl)benzothiazolinone as a starting material, the following are obtained:

EXAMPLE 44

7-{2-[N-(4-phthalimidobutyl)-N-n-propylamino]ethyl}benzothiazolinone

EXAMPLE 45

7-{2-[N-(3-phthalimidopropyl)amino]ethyl}-benzothiazolinone

EXAMPLE 46

7-{2-[N-(3-phthalimidopropyl)-N-n-propylamino]ethyl}benzothiazolinone

EXAMPLE 47

7-{2-[N-(2-phthalimidoethyl)amino]ethyl}benzothiazolinone

EXAMPLE 48

7-{2-[N-(2-phthalimidoethyl)-N-n-propylamino]ethyl}-benzothiazolinone

EXAMPLE 49

3-[4-{N-[2-(benzothiazolinon-7-yl)ethyl]amino} butyl]-2,4-dioxo-3-azaspiro[4.5]decane

EXAMPLE 50

3-[4-{N-[2-(benzothiazolinon-7-yl)ethyl]-N-n-propylamino}butyl]-2,4-dioxo-3-azaspiro[4.5]decane

EXAMPLE 51

3-[4-{N-[2-(benzothiazolinon-7-yl)ethyl]amino} butyl]-2,4-dioxo-3-azabicyclo[3.3.0]octane

EXAMPLE 52

7-[2-{N-[4-(4,4-dimethyl-2,6-dioxo-1-piperidyl)butyl]amino}ethyl]benzothiazolinone

EXAMPLE 53

7-[2-{N-[4-(4,4-dimethyl-2-oxo-1-piperidyl)butyl]amino}ethyl]benzothiazolinone

EXAMPLE 54

7-[2-{N-[4-(2-oxo-1-piperidyl)butyl]amino}ethyl]benzothiazolinone

EXAMPLE 55

4-Methyl-7-(4-aminobutyl)-2,3-dihydro-3-oxo-1,4-benzoxazine

Employing 4-methyl-7-(4-bromobutyl)-2,3-dihydro-3-oxobenzoxazine in Example 1 instead of 3-methyl-6-(2-bromoethyl)benzothiazolinone, the product of the title is obtained.

EXAMPLES 56 TO 67

Using the procedure described in Examples 2 to 13, but employing 7-(4-aminobutyl)-4-methyl-2,3-dihydro-3-oxobenzoxazine instead of 3-methyl-6-(2-bromoethyl)benzothiazolinone, the following are obtained:

EXAMPLE 56

4-Methyl-7-{4-[N-(4-phthalimidobutyl)amino]butyl}-2,3-dihydro-3-oxo-1,4-benzoxazine

EXAMPLE 57

4-Methyl-7-{4-[N-(4-phthalimidobutyl)-N-n-propylamino]butyl}-2,3-dihydro-3-oxo-1,4-benzoxazine

EXAMPLE 58

4-Methyl-7-{4-[N-(3-phthalimidopropyl)amino]-butyl}-2,3-dihydro-3-oxo-1,4-benzoxazine

EXAMPLE 59

4-Methyl-7-{4-[N-(3-phthalimidopropyl)-N-n-propylamino]-butyl}-2,3-dihydro-3-oxo-1,4-benzoxazine

EXAMPLE 60

4-Methyl-7-{4-[N-(2-phthalimidoethyl)amino]butyl}-2,3-dihydro-3-oxo-1,4-benzoxazine

EXAMPLE 61

4-Methyl-7-{4-[N-(2-phthalimidoethyl)-N-n-propylamino]butyl}-2,3-dihydro-3-oxo-1,4-benzoxazine

EXAMPLE 62

3-[4-{N-[4-(4-methyl-2,3-dihydro-3-oxo-1,4-benzoxazin-7-yl)butyl]amino}butyl]-2,4-dioxo-3-azaspiro[4.5]-decane

EXAMPLE 63

3-[4-{N-[4-(4-methyl-2,3-dihydro-3-oxo-1,4-benzoxazin-7-yl)butyl]-N-n-propylamino}butyl]-2,4-dioxo-3-azaspiro-[4.5]decane

EXAMPLE 64

3-[4-{N-[4-(4-methyl-2,3-dihydro-3-oxo-1,4-benzoxazin-7-yl)butyl]amino}butyl]-2,4-dioxo-3-azabicyclo[3.3.0]-octane

EXAMPLE 65

4-Methyl-7-[4-{N-[4-(4,4-dimethyl-2,6-dioxo-1-piperidyl)butyl]amino}butyl]-2,3-dihydro-3-oxo-1,4-benzoxazine

EXAMPLE 66

4-Methyl-7-[4-{N-[4-(4,4-dimethyl-2-oxo-1-piperidyl)butyl]amino}butyl]-2,3-dihydro-3-oxo-1,4-benzoxazine

EXAMPLE 67

4-Methyl-7-[4-{N-[4-(2-oxo-1-piperidyl)butyl]amino}-butyl]-2,3-dihydro-3-oxo-1,4-benzoxazine

EXAMPLES 68 TO 71

Employing as in Examples 14 to 17 4-methyl-7-(4-bromobutyl)-2,3-dihydro-3-oxo-1,4-benzoxazine as a starting material instead of 3-methyl-6-(2-bromoethyl)-benzothiazolinone, the following is obtained:

EXAMPLE 68

4-Methyl-7-[4-(N-methyl-N-benzylamino)butyl]-2,3-dihydro-3-oxo-1,4-benzoxazine which on catalytic hydrogenation yields:

EXAMPLE 69

4-Methyl-7-[4-(N-methylamino)butyl]-2,3-dihydro-3-oxo-1,4-benzoxazine

EXAMPLE 70

4-Methyl-7-[4-(isopropylaminobutyl)-2,3-dihydro-3-oxo-1,4-benzoxazine

EXAMPLE 71

4-Methyl-7-[4-n-propylaminobutyl)-2,3-dihydro-3-oxo-1,4-benzoxazine

EXAMPLE 72

4-Methyl-7-[4-(N-methyl-N-cyanomethylamino)butyl]-2,3-dihydro-3-oxo-1,4-benzoxazine Using the procedure described in Example 18, but replacing 3-methyl-6-[2-(N-methylamino)ethyl]benzothiazolinone by 4-methyl-7-[4-(N-methylamino)butyl]-2,3-dihydro-3-oxo-1,4-benzoxazine, the product of the title is obtained.

Using the procedure described in Examples 19 and 20 with the product of Example 72, the following are obtained:

EXAMPLE 73

4-Methyl-7-{4-[N-methyl-N-(2-aminoethyl)amino]-butyl}-2,3-dihydro-3-oxo-1,4-benzoxazine

EXAMPLE 74

4-Methyl-7-[4-{N-methyl-N-[2-(para-tolylsulfonylamino)ethyl]amino}butyl]-2,3-dihydro-3-oxo-1,4-benzoxazine

EXAMPLE 75

4-Methyl-7-[4-{N-n-propyl-N-[3-(para-tolylsulfonylamino)propyl]amino}butyl]-2,3-dihydro-3-oxo-1,4-benzoxazine Using the procedure described in Example 24, but replacing 3-methyl-6-(2-propylaminoethyl)benzothiazolinone by 4-methyl-7-(4-propylaminobutyl)-2,3-dihydro-3-oxo-1,4-benzoxazine, the product of the title is obtained.

EXAMPLE 76

4-Methyl-7-[4-{N-n-propyl-N-[4-(para-tolylsulfonylamino)butyl]amino}butyl]-2,3-dihydro-3-oxo-1,4-benzoxazine Using the procedure described in Example 75, but replacing 1-chloro-3-bromopropane by 1-chloro-4-bromobutane, the product of the title is obtained.

EXAMPLE 77

7-(2-Aminoethyl)-3-oxo-2,3-dihydro-1,4-benzoxazine

In a 250-$cm^3$ ground-necked flask, 0.01 mol of 7-(2-bromoethyl)-3-oxo-2,3-dihydro-1,4-benzoxazine and 0.3 g of potassium iodide are dissolved in 30 $cm^3$ of dimethylformamide.

A stream of gaseous ammonia is bubbled into the solution to the point of saturation and a reflux condenser is fitted. The temperature is stabilized at 50° C. with an oil bath and the mixture is then left stirring magnetically for 72 hours. After cooling, the reaction mixture is evaporated on a water bath under vacuum. The residue is ground in distilled water acidified with 5% HCl solution, and then drained. The filtrate is recovered, washed with ethyl acetate and then alkalinized with 10% sodium hydroxide solution. It is extracted with chloroform, leaving the 2 phases agitating for 1/2 hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized.

EXAMPLE 78

4-Methyl-7-(2-propylaminoethyl)-3-oxo-2,3-dihydro-1,4-benzoxazine

Using the procedure described in Preparation 9, but replacing 6-(2-bromoethyl)-3-oxo-2,3-dihydro-1,4-benzoxazine by 4-methyl-7-(2-bromoethyl)-3-oxo-2,3-dihydro-1,4-benzoxazine, the product of the title is obtained.

EXAMPLES 79 TO 90

Using the procedure described in Examples 2 to 13, but employing 7-(2-aminoethyl)-4-methyl-3-oxo-2,3-dihydro-1,4-benzoxazine instead of 3-methyl-6-(2-bromoethyl)benzothiazolinone, the following are obtained:

EXAMPLE 79

4-Methyl-7-{2-[N-(4-phthalimidobutyl)amino]ethyl}-3-oxo-2,3-dihydro-1,4-benzoxazine

EXAMPLE 80

4-Methyl-7-{2-[N-(4-phthalimidobutyl)-N-n-propylamino]ethyl}-3-oxo-2,3-dihydro-1,4-benzoxazine

EXAMPLE 81

4-Methyl-7-{2-[N-(3-phthalimidopropyl)amino]ethyl}-3-oxo-2,3-dihydro-1,4-benzoxazine

EXAMPLE 82

4-Methyl-7-{2-[N-(3-phthalimidopropyl)-N-n-propylamino]ethyl}-3-oxo-2,3-dihydro-1,4-benzoxazine

EXAMPLE 83

4-Methyl-7-{2-[N-(2-phthalimidoethyl)amino]ethyl}-3-oxo-2,3-dihydro-1,4-benzoxazine

EXAMPLE 84

4-Methyl-7-{2-[N-(2-phthalimidoethyl)-N-n-propylamino]ethyl}-3-oxo-2,3-dihydro-1,4-benzoxazine

EXAMPLE 85

3-[4-{N-[2-(4-methyl-3-oxo-2,3-dihydro-1,4-benzoxazin-7-yl)ethyl]amino}butyl]-2,4-dioxo-3-azaspiro[4.5]-decane

EXAMPLE 86

3-[4-{N-[2-(4-methyl-3-oxo-2,3-dihydro-1,4-benzoxazin-7-yl)ethyl]-N-n-propylamino}butyl]-2,4-dioxo-3-azaspiro[4.5]decane

EXAMPLE 87

3-[4-{N-[2-(4-methyl-3-oxo-2,3-dihydro-1,4-benzoxazin-7-yl)ethyl]amino}butyl]-2,4-dioxo-3-azabicyclo[3.3.0]octane

EXAMPLE 88

4-Methyl-7-[2-{N-[4-(4,4-dimethyl-2,6-dioxo-1-piperidyl)-butyl]amino}ethyl]-3-oxo-2,3-dihydro-1,4-benzoxazine

EXAMPLE 89

4-Methyl-7-[2-{N-[4-(4,4-dimethyl-2-oxo-1-piperidyl)-butyl]amino}ethyl]-3-oxo-2,3-dihydro-1,4-benzoxazine

EXAMPLE 90

4-Methyl-7-[2-{N-[4(2-oxo-1-oxo1-piperidyl)-butyl-]amino}-ethyl]-3-oxo-2,3-dihydro-1,4-benzoxazine

EXAMPLE 91

4-Methyl-7-[2-{N-propyl-N-cyanomethylamino}-ethyl]-3-oxo-2,3-dihydro-1,4-benzoxazine Using the procedure described in Example 18, but replacing 3-methyl-6-[2-(N-methylamino)ethyl]benzothiazolinone by 4-methyl-7-[2-(N-propylamino)ethyl]-3-oxo-2,3-dihydro-1,4-benzoxazine, the product of the title is obtained.

Using the procedure described in Examples 19 and 20 with the product of Example 91, the following are obtained, respectively:

EXAMPLE 92

4-Methyl-7-{2-[N-propyl-N-(2-aminoethyl)amino]ethyl}-3-oxo-2,3-dihydro-1,4-benzoxazine

EXAMPLE 93

4-Methyl-7-[2-{N-propyl-N-[2-(para-tolylsulfonylamino)-ethyl]amino}ethyl]-3-oxo-2,3-dihydro-1,4-benzoxazine

EXAMPLE 94

4-Methyl-7-[2-{N-propyl-N-[3-(para-tolylsulfonylamino)-propyl]amino}ethyl]-3-oxo-2,3-dihydro-1,4-benzoxazine Using the procedure described in Example 24, but replacing 3-methyl-6-(2-propylaminoethyl)benzothiazolinone by 4-methyl-7-(2-propylaminoethyl)-3-oxo-2,3-dihydro-1,4-benzoxazine, the product of the title is obtained.

EXAMPLE 95

4-Methyl-7-[2-{N-propyl-N-[4-(para-tolylsulfonylamino)-butyl]amino}ethyl]-3-oxo-2,3-dihydro-1,4-benzoxazine Using the procedure described in Example 94, but replacing 1-chloro-3-bromopropane by 1-chloro-4-bromobutane, the product of the title is obtained.

EXAMPLE 96

6-(2-Aminoethyl)-3-oxo-2,3-dihydro-1,4-benzoxazine

In a 250-$cm^3$ ground-necked flask, 0.01 mol of 6-(2-bromoethyl)-3-oxo-2,3-dihydro-1,4-benzoxazine and 0.3 g of potassium iodide are dissolved in 30 $cm^3$ of dimethylformamide.

A stream of gaseous ammonia is bubbled into the solution to the point of saturation and a reflux condenser is fitted. The temperature is stabilized at 50° C. with an oil bath and the mixture is then left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is passed through and the mixture is then evaporated to dryness on a water bath under vacuum. The product is dried and then recrystallized.

EXAMPLES 97 TO 109

Using the procedure described in Examples 2 to 13, but employing 6-(2-aminoethyl)-3-oxo-2,3-dihydro-1,4-benzoxazine instead of 3-methyl-6-(2-bromoethyl)benzothiazolinone, the following are obtained:

EXAMPLE 97

6-{2-[N-(4-phthalimidobutyl)amino]ethyl}-3-oxo-2,3-dihydro-1,4-benzoxazine

EXAMPLE 98

6-{2-[N-(4-phthalimidobutyl)-N-n-propylamino]ethyl}-3-oxo-2,3-dihydro-1,4-benzoxazine

EXAMPLE 99

6-{2-[N-(3-phthalimidopropyl)amino]ethyl}-3-oxo-2,3-dihydro-1,4-benzoxazine

EXAMPLE 100

6-{2-[N-(3-phthalimidopropyl)-N-n-propylamino]ethyl}-3-oxo-2,3-dihydro-1,4-benzoxazine

EXAMPLE 101

6-{2-[N-(2-phthalimidoethyl)amino]ethyl}-3-oxo-2,3-dihydro-1,4-benzoxazine

EXAMPLE 102

6-{2-[N-(2-phthalimidoethyl)-N-n-propylamino]ethyl}-3-oxo-2,3-dihydro-1,4-benzoxazine

EXAMPLE 103

3-[4-{N-[2-(3-oxo-2,3-dihydro-1,4-benzoxazin-6-yl)-ethyl]amino}butyl]-2,4-dioxo-3-azaspiro[4.5]decane

EXAMPLE 104

3-[4-{N-[2-(3-oxo-2,3-dihydro-1,4-benzoxazin-6-yl)-ethyl]-N-n-propylamino}butyl]-2,4-dioxo-3-azaspiro[4.5]decane

EXAMPLE 105

3-[4-{N-[2-(3-oxo-2,3-dihydro-1,4-benzoxazin-6-yl)-ethyl]amino}butyl]-2,4-dioxo-3-azabicyclo[3.3.0]octane

EXAMPLE 106

6-[2-{N-[4-(4,4-dimethyl-2,6-dioxo-1-piperidyl)-butyl]-amino}ethyl]-3-oxo-2,3-dihydro-1,4-benzoxazine

EXAMPLE 107

6-[2-{N-[4-(4,4-dimethyl-2-oxo-1-piperidyl)butyl-]amino}-ethyl]-3-oxo-2,3-dihydro-1,4-benzoxazine

EXAMPLE 108

6-[2-{N-[4-(2-oxo-1-piperidyl)butyl]amino}ethyl]-3-oxo-2,3-dihydro-1,4-benzoxazine

EXAMPLE 109

6-[2-(N-methyl-N-cyanomethylamino)ethyl]-3-oxo-2,3-dihydro-1,4-benzoxazine

Using the procedure described in Example 17, but replacing 3-methyl-6-[2-(N-methylamino)ethyl]benzothiazolinone by 6-[2-(N-methylamino)ethyl]-3-oxo-2,3-dihydro-1,4-benzoxazine, the product of the title is obtained.

Using the procedure described in Examples 18 and 19 with the product of Example 109, the following are obtained:

EXAMPLE 110

6-{2-[N-propyl-N-(2-aminoethyl)amino]ethyl}-3-oxo-2,3-dihydro-1,4-benzoxazine

EXAMPLE 111

6-[2-{N-propyl-N-[2-(para-tolylsulfonylamino)ethyl-]amino}ethyl]-3-oxo-2,3-dihydro-1,4-benzoxazine

EXAMPLE 112

6-[2-{N-n-propyl-N-[3-(para-tolylsulfonylamino)-propyl]-amino}ethyl]-3-oxo-2,3-dihydro-1,4-benzoxazine Using the procedure described in Example 24, but replacing 3-methyl-6-(2-propylaminoethyl)benzothiazolinone by 6-(2-propylaminoethyl)-3-oxo-2,3-dihydro-1,4-benzoxazine, the product of the title is obtained.

EXAMPLE 113

6-[2-{N-n-propyl-N-[4-(para-tolylsulfonylamino)butyl]-amino}ethyl]-3-oxo-2,3-dihydro-1,4-benzoxazine Using the procedure described in Example 112, but replacing 1-chloro-3-bromopropane by 1-chloro-4-bromobutane, the product of the title is obtained.

EXAMPLE 114

3-Methyl-6-[2-{N-[4-(3-oxo-2,3-dihydro-2-benzisothiazolyl 1,1-dioxide)butyl]amino}ethyl]benzothiazolinone Replacing N-(4-bromobutyl)phthalimide in Example 2 by 3-oxo-2,3-dihydro-2-(4-bromobutyl)benisothiazole 1,1-dioxide, the product of the title is obtained.

EXAMPLE 115

3-Methyl-6-[2-{N-[4-(3-oxo-2,3-dihydro-2-benzisothiazolyl 1,1-dioxide)butyl]-N-n-propylamino}ethyl]benzothiazolinone Using the procedure described in Example 3, but employing the product obtained in Example 114 instead of 3-methyl-6-{2-[N-(4-phthalimidobutyl)amino]ethyl} benzothiazolinone, the product of the title is obtained.

EXAMPLE 116

3-Methyl-6-[2-{N-[3-(3-oxo-2,3-dihydro-2-benzisothiazolyl 1,1-dioxide)propyl]amino}ethyl]benzothiazolinone By replacing N-(4-bromobutyl)phthalimide in Example 2 by 3-oxo-2,3-dihydro-2-(3-bromopropyl)benzisothiazole 1,1-dioxide, the product of the title is obtained.

EXAMPLE 117

3-Methyl-6-[2-{N-[3-(3-oxo-2,3-dihydro-2-benzisothiazolyl 1,1-dioxide)propyl]-N-n-propylamino}ethyl]-benzothiazolinone Using the procedure described in Example 3, but employing the product obtained in Example 116 instead of 3-methyl-6-{2-[N-(4-phthalimidobutyl)amino]ethyl} benzothiazolinone, the product of the title is obtained.

EXAMPLE 118

3-Methyl-6-[2-{N-[2-(3-oxo-2,3-dihydro-2-benzisothiazolyl 1,1-dioxide)ethyl]amino}ethyl]benzothiazolinone By replacing N-(4-bromobutyl)phthalimide in Example 2 by 3-oxo-2,3-dihydro-2-(2-bromoethyl)-benzisothiazole 1,1-dioxide, the product of the title is obtained.

EXAMPLE 119

3-Methyl-6-[2-{N-[2-(3-oxo-2,3-dihydro-2-benzisothiazolyl 1,1-dioxide)ethyl]-N-n-propylamino}ethyl]benzothiazolinone Using the procedure described in Example 3, but employing the product obtained in Example 118 instead of 3-methyl-6-{2-[N-(4-phthalimidobutyl)amino]ethyl} benzothiazolinone, the product of the title is obtained.

EXAMPLE 120

3-Methyl-6-(4-aminobutyl)benzoxazolinone (hydrochloride)

Using the procedure described in Example 1, but replacing 3-methyl-6-(2-bromoethyl)benzothiazolinone by 3-methyl-6-(4-chlorobutyl)benzothiazolinone, 3-methyl-6-(4-aminobutyl)benzothiazolinone (hydrochloride) is obtained.

EXAMPLES 121 to 132

Using the procedure described in Examples 2 to 13, but replacing 3-methyl-6-(2-aminoethyl)benzothiazolinone by 3-methyl-6-(4-aminobutyl)benzoxazolinone of Example 120, the following are obtained:

EXAMPLE 121

3-Methyl-6-{4-[N-(4-phthalimidobutyl)amino]butyl}-benzoxazolinone

EXAMPLE 122

3-Methyl-6-{4-[N-(4-phthalimidobutyl)-N-n-propylamino]-butyl}benoxazolinone

EXAMPLE 123

3-Methyl-6-{4-[N-(3-phthalimidopropyl)amino]-butyl}-benoxazolinone

EXAMPLE 124

3-Methyl-6-{4-[N-(3-phthalimidopropyl)-N-propylamino]butyl}-benoxazolinone

EXAMPLE 125

3-Methyl-6-{4-[N-(2-phthalimidoethyl)-N-n-propylamino]butyl}-benoxazolinone

EXAMPLE 126

3-Methyl-6-{4-[N-(2-phthalimidoethyl)amino]butyl}-benoxazolinone

EXAMPLE 127

3-[4-{N-[4-(3-methylbenzoxazolinon-6-yl)butyl-]amino}-butyl]-2,4-dioxo-3-azaspiro[4.5]decane

EXAMPLE 128

3-[4-{N-[4-(3-methylbenzoxazolinon-6-yl)butyl]N-n-propylamino}butyl]-2,4-dioxo-3-azaspiro[4.5]decane

EXAMPLE 129

3-[4-{N-[4-(3-methylbenzoxazolinon-6-yl)butyl-]amino}-butyl]-2,4-dioxo-3-azabicyclo[3.3.0]octane

EXAMPLE 130

3-Methyl-6-[4-{N-[4-(4,4-dimethyl-2,6-dioxo-1-piperidyl)-butyl]amino}butyl]benzoxazolinone

EXAMPLE 131

3-Methyl-6-[4-{N-[4-(4,4-dimethyl-2-oxo-1-piperidyl)butyl]amino}butyl]benzoxazolinone

EXAMPLE 132

3-Methyl-6-[4-{N-[4-(2-oxo-1-piperidyl)butyl-]amino}-butyl]benzoxazolinone

EXAMPLES 133 to 144

Using the procedure described in Examples 2 to 13, but replacing 3-methyl-6-(2-aminoethyl)benzothiazolinone by 3-methyl-6-(2-aminoethyl)benzoxazolinone described in Application EP 110,781, the following are obtained:

EXAMPLE 133

3-Methyl-6-{4-[N-(4-phthalimidobutyl)amino]ethyl}-benzoxazolinone

EXAMPLE 134

3-Methyl-6-{4-[N-(4-phthalimidobutyl)-N-n-propylamino]ethyl}benzoxazolinone

EXAMPLE 135

3-Methyl-6-{4-[N-(3-phthalimidopropyl)amino]e-thyl}benzoxazolinone

EXAMPLE 136

3-Methyl-6-{4-[N-(3-phthalimidopropyl)-N-propylamino]ethyl}benzoxazolinone

EXAMPLE 137

3-Methyl-6-{4-[N-(2-phthalimidoethyl)-N-n-propylamino]ethyl}benzoxazolinone

EXAMPLE 138

3-Methyl-6-{4-[N-(2-phthalimidoethyl)amino]ethyl} benzoxazolinone

EXAMPLE 139

3-[4-{N-[4-(3-methylbenzoxazolinon-6-yl)ethyl-]amino}-butyl]-2,4-dioxo-3-azaspiro[4.5]decane

EXAMPLE 140

3-[4-{N-[4-(3-methylbenzoxazolinon-6-yl)ethyl]-N-n-propylamino}butyl]-2,4-dioxo-3-azaspiro[4.5]decane

EXAMPLE 141

3-[4-{N-[4-(3-methylbenzoxazolinon-6-yl)ethyl-]amino}butyl]-2,4-dioxo-3-azabicyclo[3.3.0]octane

EXAMPLE 142

3-Methyl-6-[4-{N-[4-(4,4-dimethyl-2,6-dioxo-1-piperidyl)-butyl]amino}ethyl]benzoxazolinone

EXAMPLE 143

3-Methyl-6-[4-{N-[4-(4,4-dimethyl-2-oxo-1-piperidyl)-butyl]amino}ethyl]benzoxazolinone

EXAMPLE 144

3-Methyl-6-[4-{N-[4-(2-oxo-1-piperidyl)butyl-]amino}-ethyl]benzoxazolinone

EXAMPLE 145

3-[4-{N-methyl-N-[2-(3-methylbenzothiazolinon-6-yl)-ethyl]amino}butyl]-2,4-dioxo-3-azaspiro[4.5]decane-hydrochloride In a ground-necked flask surmounted by a reflux condenser, $10^{-2}$ mol of 3-methyl-6-[2-(N-methylamino)ethyl]benzoxazolinone, obtained in Example 15, and $1.2\times10^{-2}$ mol of triethylamine are dissolved in acetone, and the mixture is brought to reflux for 15 minutes. 0.02 mol of N-(4-bromobutyl)-2,4-dioxo-3-azaspiro[4.5]-decane is added and refluxing is maintained for 24 hours. The precipitate formed is drained, the filtrate is evaporated to dryness, the residue is taken up with dilute hydrochloric acid solution, the acidic medium is washed with toluene and then, after alkalinization, the aqueous phase is extracted several times with chloroform.

The organic phases are combined and evaporated to dryness, the residue is taken up with anhydrous ether and the requisite amount of ethereal hydrogen chloride is added. The product is drained, dried and recrystallized.

Yield: 35%

Melting point: 173°-174° C.

Spectral characteristics:

Infrared: 1600-1680 $cm^{-1}$: $\nu$CO. 1750 $cm^{-1}$: $\nu$CO (SCON).

1H Nuclear Magnetic Resonance: 2.60 ppm, singlet: 4H 2($NCH_2CO$). 2.80 ppm, singlet: 3H (amine). 3.50 ppm, singlet: 3H (amide).

EXAMPLE 146

3-[4-{N-methyl-N-[2-(3-methylbenzothiazolinon-6-yl)-ethyl]amino}butyl]-2,4-dioxo-3-azabicyclo[3.3.0]octane hydrochloride Using the procedure described in Example 145, but replacing N-(4-bromobutyl)2,4-dioxo-3-azaspiro[4.5]-decane by N-(4-bromobutyl)-2,4-dioxo-3-azabicyclo-[3.3.0]octane, the product of the title is obtained.

Yield: 45%

Melting point: 130°-132° C.

Spectral characteristics:

Infrared: 1600-1700 $cm^{-1}$: $\nu$CO. 1760 $cm^{-1}$: $\nu$CO (SCON).

1H Nuclear Magnetic Resonance: 2.80 ppm, singlet: 3H ($CH_3$).

EXAMPLE 147

3-[4-{N-methyl-N-[4-(3-methylbenzothiazolinon-6-yl)-butyl]amino}butyl]-2,4-dioxo-3-azaspiro[4.5]decane hydrochloride Using the procedure described in Example 145, but replacing 3-methyl-6-[2-(N-methylamino)ethyl]benzothiazolinone by 3-methyl-6-[4-(N-methylamino)butyl]-benzothiazolinone, obtained in Example 38, the product of the title is obtained.

EXAMPLE 148

3-[4-{N-methyl-N-[4-(3-methylbenzothiazolinon-6-yl)-butyl]amino}butyl]-2,4-dioxo-3-azabicyclo[3.3.0]octane hydrochloride Using the procedure described in Example 146, but replacing 6-[2-(N-methylamino)ethyl]benzothiaoxazolinone by 6-[4-(N-methylamino)butyl]benzothiazolinone, the product of the title is obtained.

EXAMPLE 149

3-[3-{N-methyl-N-[2-(3-methylbenzothiazolinon-6-yl)ethyl]-amino}propyl]-2,4-dioxo-3-azabicyclo[4.5]decane hydrochloride Using the procedure described in Example 145, but replacing N-(4-bromobutyl)-2,4-dioxo-3-azaspiro[4.5]-decane by N-(3-bromopropyl)-2,4-dioxo-3-azaspiro[4.5]-decane, the product of the title is obtained.

EXAMPLE 150

3-[3-{N-methyl-N-[2-(3-methylbenzothiazolinon-6-yl)ethyl]amino}propyl]-2,4-dioxo-3-azabicyclo[3.3.0]octane hydrochloride Using the procedure described in Example 146, but replacing N-(4-bromobutyl)-2,4-dioxo-3-azabicyclo[3.3.0]-octane by N-(3-bromopropyl)-2,4-dioxo-3-azabicyclo[3.3.0]octane, the product of the title is obtained.

PHARMACOLOGICAL STUDY OF THE COMPOUNDS OF THE INVENTION

EXAMPLE 151

In Vitro Affinity Test for $5\text{-HT}_{1A}$, $D_2$ and $\alpha_2$ Receptors

The in vitro affinity tests for $5\text{-HT}_{1A}$, $D_2$ and $\alpha_2$ receptors were carried out according to conventional binding techniques.

The results of these studies show that the compounds of the invention possess a K0.5 of the order of $10^{-10}$M with respect to $5\text{-HT}_{1A}$ receptors. This very great affinity is complemented by a very great selectivity. In effect, the ratio of the $5\text{-HT}_{1A}$/D2 affinities is equal to 100. That of the $5\text{-HT}_{1A}/\alpha 2$ affinities is equal to $10^4$.

EXAMPLE 152

Acute Toxicity

The acute toxicity was assessed after oral administration of a dose of 650 $mg.kg^{-1}$ to batches of 8 mice (26±2 grams). The animals were observed at regular intervals during the first day and daily during the two weeks following the treatment.

It is apparent that most of the compounds of the invention are completely non-toxic. Most of them cause no deaths after administration at a dose of 650 $mg.kg^{-1}$, and no disorders are generally observed after administration of this dose.

EXAMPLE 153

Study of Anxiolytic Activity—Pigeon Conflict Test

Six White Carneaux pigeons not previously used in experiments are trained to peck a Plexiglass key which is transilluminated by red or white lights. The response key is mounted on the front wall of the experimental chamber. The pigeons are brought to 85% of their normal weight before the beginning of the experiment, which is carried out using the method of successive approximations (Frester 1953). At the start, each peck of the key (illuminated with a red or white light) which exceeds a force of 0.15N permits access to a mixture of cereals via an automatic dispenser located under the key. After several days, the cereals are no longer delivered until the thirtieth peck on the key. When this response to the 30th strike is obtained, and when it occurs regularly, permitting the delivery of feed, the color of the light of the key is alternated every three minutes (from white to red and vice versa). The measurement of the level of response to the 30th strike remains operative during each light phase.

During this phase and throughout the experiment, a daily session is composed of 5 cycles of 3 minutes of each light sequence, these sequences being separated by a 30-second interval during which the luminous keys are extinguished and the responses have no effect. Consequently, a sequence lasts approximately 35 to 40 minutes. When these levels of responses are stable and indentical for each color during a period of 5 days (this requires 3 to 4 weeks), every 30th response in one of the colored phases simultaneously brings about a release of feed and a brief (200-millisecond) and moderate (1.3 mA) electric shock delivered by electrodes placed on the pubic pones. The level of reponses is reduced at first, then returns to the initial value.

The administration of the products of the invention is carried out after a stable level of response is obtained over a period of 5 days.

The intramuscular injection of the products of the invention at a dose of 0.3 $mg/kg^{-1}$ brings about a significant increase in responses whether or not followed by electric shocks, demonstrating the anxiolytic activity of these products.

EXAMPLE 154

Pharmaceutical Compositions

Tablets intended for the treatment of conditions affecting the mind, containing 5 mg of 3-[4-{N-[2-(3-methylbenzothiazolinon-6-yl)ethyl]amino}butyl]-2,4-dioxo-3-azaspiro[4.5]decane.

| Preparation formula for 1,000 tablets. | |
|---|---|
| 3-[4-{N-[2-(3-Methylbenzothiazolinon-6-yl)ethyl] amino-butyl]-2,4-dioxo-3-azaspiro[4.5]decane | 5 g |
| Wheat starch | 20 g |
| Corn starch | 20 g |
| Lactose | 65 g |
| Magnesium stearate | 2 g |
| Silica | 1 g |
| Hydroxypropylcellulose | 2 g |

Tablets intended for the treatment of pain, containing 2,5 mg of 3-methyl-6-{2-[4-(3-trifluoromethyl-phenyl)-1-piperazinyl]ethyl}benzothiazolinone hydrochloride.

| Preparation formula for 1,000 tablets | |
|---|---|
| 3-Methyl-6-{2-[4-(3-trifluoromethylphenyl)-1-piperazinyl] ethyl}benzothiazolinone hydrochloride | 2,5 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

We claim:

1. A compound selected from those of formula (I):

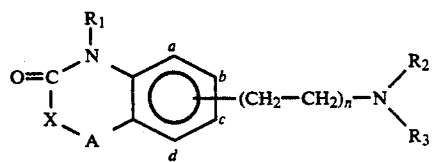

in which:

$R_1$ represents hydrogen or lower alkyl, n represents 1 or 2,

A represents oxygen or sulfur,

X represents a $CH_2$ group, $R_2$ represents hydrogen or lower alkyl or lower acyl and $R_3$ represents $(CH_2)pR_4$, with p being an integer from 1 and 6, inclusive, and $R_4$ represents:

a nitrile group, in which case $R_3$ represents $(CH_2)_{p-1}R_4$, or halogen or amino optionally substituted with:

(lower alkyl) sulfonyl, phenylsulfonyl optionally substituted on the phenyl ring with one or more lower alkyl, lower alkoxy, hydroxyl, or trifluoromethyl groups or a halogen atom, one or two ($C_1$-$C_6$) acyl groups optionally substituted with a lower alkyl, lower alkoxy, or hydroxyl group, a halogen atom, or a phenyl, thienyl, benzothienyl, indolyl, furyl, or benzofuryl group, the phenyl, thienyl, benzo-thienyl, indolyl, furyl and benzofuryl groups themselves optionally being substituted with one or more lower alkyl, lower alkoxy, or hydroxyl groups or a halogen atom, one or two linear or branched ($C_1$-$C_6$) alkyl groups, or $R_4$ represents any one of the following groups:

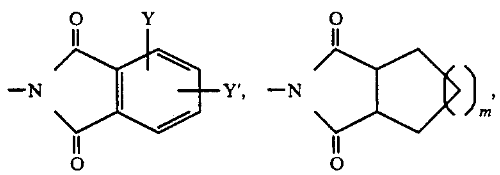

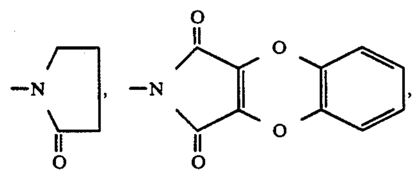

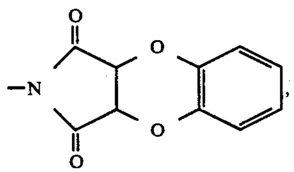

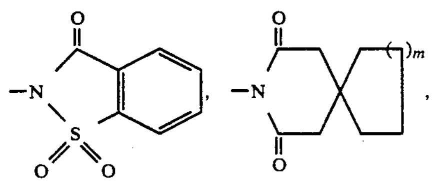

-continued

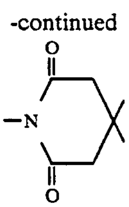

in which:

Y and Y', which may be identical or different, represent hydrogen, halogen or lower alkyl, lower alkoxy, or hydroxyl group, m is 1 or 2, its enantiomers, diastereoisomers, and epimers, and its addition salts with a pharmaceutically-acceptable acid or a pharmaceutically-acceptable base when $R_1$=H.

2. A compound selected from those of claim 1 for which $R_1$ represents a $CH_3$ group, its enantiomers, epimers and diastereoisomers and its addition salts with a pharmaceutically-acceptable acid or a pharmaceutically-acceptable base when $R_1$=H.

3. A compound selected from those of claim 1 for which A represents a sulfur atom, its enantiomers, epimers and diastereoisomers as well as its addition salts with a pharmaceutically-acceptable acid or a pharmaceutically-acceptable base when $R_1$=H.

4. A compound selected from those of claim 1 for which A represents an oxygen atom and X represents a $CH_2$ group, its enantiomers, epimers and diastereoisomers as well as its addition salts with a pharmaceutically-acceptable acid or a pharmaceutically-acceptable base when $R_1$=H.

5. A compound selected from those of claim 1 for which the group $(CH_2—CH_2)_n—NR_2R_3$ is at position b, its enantiomers, epimers and diastereoisomers as well as its addition salts with a pharmaceutically-acceptable acid or a pharmaceutically-acceptable base when $R_1$=H.

6. A compound selected from those of claim 1 for which the group $(CH_2—CH_2)_n—NR_2R_3$ is at position c, its enantiomers, epimers and diastereoisomers as well as its addition salts with a pharmaceutically-acceptable acid or a pharmaceutically-acceptable base when $R_1$=H.

7. A compound selected from those of claim 1 for which the group $(CH_2—CH_2)_n—NR_2R_3$ is at position d, its enantiomers, epimers and diastereoisomers as well as its addition salts with a pharmaceutically-acceptable acid or a pharmaceutically-acceptable base when $R_1$=H.

8. A compound selected from those of claim 1 for which X represents a $CH_2$ group, A represents a sulfur atom, n is equal to 1, and $R_3$ represents a group $(CH_2)pR_4$, with p being 1 to 6, inclusive, and $R_4$ represents:

an amino group substituted with a phenylsulfonyl group optionally substituted on the phenyl ring with one or more lower alkyl, lower alkoxy, hydroxyl, or trifluoromethyl groups or a halogen atom, or alternatively any one of the following groups:

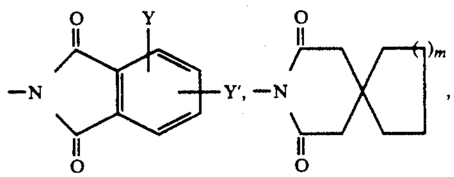

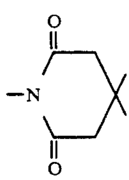

in which:

Y and Y', which may be identical or different, represent hydrogen, halogen lower alkyl, lower alkoxy, or hydroxyl, m is 1 or 2, its enantiomers, epimers and diastereoisomers and its addition salts with a pharmaceutically-acceptable acid or a pharmaceutically-acceptable base when $R_1=H$.

9. A compound as claimed in claim 1 which is selected from 3-[4-{N-[2-(4-methyl-2,3-dihydro-3-oxo-1,4-benzoxazin-7-yl)ethyl]amino}butyl]-2,4-dioxo-3-azaspiro[4.5]decane, and its addition salts with a pharmaceutically-acceptable acid.

10. A compound as claimed in claim 1 which is selected from 4-methyl-7-[2-{N-[4-(4,4-dimethyl-2,6-dioxo-1-piperidyl)butyl]amino}ethyl]-2,3-dihydro-3-oxobenzoxazine, and its addition salts with a pharmaceutically-acceptable acid.

11. A compound of claim 1 which is 4-methyl-7-{2-[N-(3-phthalimidopropyl)-N-n-propylamino]ethyl}-3-oxo-2,3-dihydro-1,4-benzoxazine of the formula

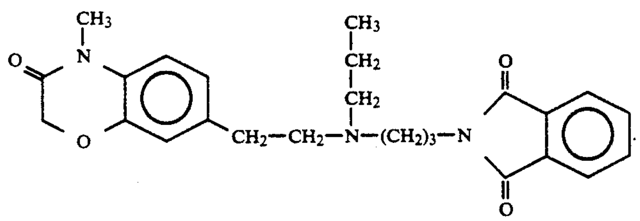

12. A compound of claim 1 which is 3-[4-{N-[2-(4-methyl-3-oxo-2,3-dihydro-1,4-benzoxazin-7-yl)ethyl]amino}butyl]-2,4-dioxo-3-azabicyclo[3.3.0]octane of the formula

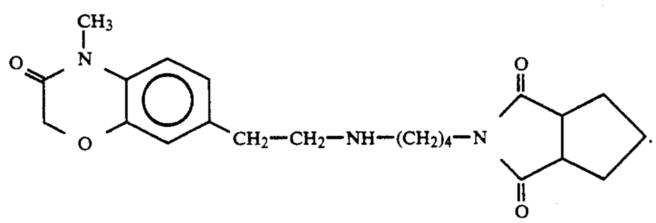

13. A compound of claim 1 which is 4-methyl-7-{4-[N-(2-phthalimidoethyl)amino]butyl}-2,3-dihydro-3-oxo-1,4-benzoxazine of the formula

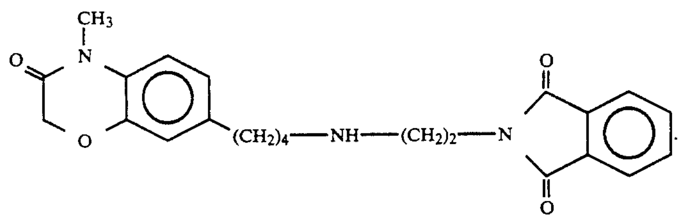

14. A compound of claim 1 which is 4-methyl-7-[4-{N-methyl-N-[2-(para-tolylsulfonylamino)ethyl]amino}butyl]-2,3-dihydro-3-oxo1,4-benzoxazine of the formula

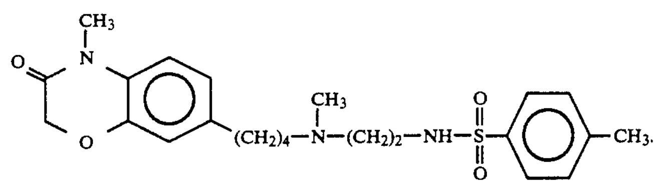

15. A pharmaceutical composition containing as active principle an effective antidepressive or anxiolytic amount of a $5\text{-HT}_{1A}$ agonist, being at least one compound as claimed in claim 1, in combination with one or more pharmaceutically-acceptable excipients or vehicles.

16. A method for treating a mammal afflicted with a condition requiring for its treatment an antidepressive or anxiolytic amount of a $5\text{-HT}_{1A}$ receptor agonist comprising the step of administering to the said mammal an amount of a compound of claim 1 which is effective for alleviation of said conditions.

* * * * *

UNITED STATES PATENT AND TRADEMARK OFFICE

CERTIFICATE OF CORRECTION

PATENT NO. : 5,296,477

DATED : Mar. 22, 1994

INVENTOR(S) : Thierry Taverne, Isabelle Lesieur, Patrick Depreux Daniele H. Caignard, Bèatrice Guardiola, Gèrard Adam, Pierre Renard It is certified that error appears in the above-indentified patent and that said Letters Patent is hereby corrected as shown below:

Column 13, line 12; underline "$CH_3$".
Column 13, line 31, 32; delete the second occurrence of "-(N-methylamino)ethyl] benzothiazolinone".
Column 14, line 51, 52; move the "e" from the end of line 51 to the beginning of line 52 and insert before "thyl".
Column 21, line 3; "[4(2-oxo-1-oxol-piperidyl)" should read -- [4-(2-oxo-1-piperidyl)-.

Signed and Sealed this

Twenty-fifth Day of October, 1994

Attest:

BRUCE LEHMAN

Attesting Officer

*Commissioner of Patents and Trademarks*